United States Patent [19]

Amemiya

[11] Patent Number: 4,693,319

[45] Date of Patent: Sep. 15, 1987

[54] CORRELATION DETECTION TYPE ULTRASOUND BLOOD FLOWMETER

[75] Inventor: Shinichi Amemiya, Yokohama, Japan

[73] Assignee: Fujitsu Limited, Kawasaki, Japan

[21] Appl. No.: 782,921

[22] Filed: Oct. 2, 1985

[30] Foreign Application Priority Data

Oct. 8, 1984 [JP] Japan .................................. 59-210800

[51] Int. Cl.[4] ............................................. A61B 10/00
[52] U.S. Cl. ................................. 128/663; 73/861.25; 73/861.27
[58] Field of Search ............................... 128/660–661, 128/663; 73/861.06, 861.25, 861.27; 367/40, 42, 100; 364/821

[56] References Cited

U.S. PATENT DOCUMENTS

| | | | |
|---|---|---|---|
| 3,334,622 | 8/1967 | Brech | 128/660 |
| 3,762,221 | 10/1973 | Coulthard | 73/861.05 |
| 4,181,134 | 1/1980 | Mason et al. | 128/689 |
| 4,265,126 | 5/1981 | Papadofrangakis et al. | 128/663 X |
| 4,417,584 | 11/1983 | Cathignol et al. | 128/663 |
| 4,484,478 | 11/1984 | Härkönen | 73/861.06 |
| 4,555,947 | 12/1985 | Van Prooijen | 73/861.06 |
| 4,573,477 | 3/1986 | Namekawa et al. | 128/663 |

OTHER PUBLICATIONS

Massen, R., "Interference-Free Acquisition of Process Data with a New Digital Correlator", Process Automation No. 1, 1982, pp. 38–42.
Winter, D. C. et al, "Ultrasonic Detection of Cardiovascular Flow Disturbances", ISA Transactions, vol. 15, No. 3, pp. 237–241, 1976.

*Primary Examiner*—Kyle L. Howell
*Assistant Examiner*—Francis J. Jaworski
*Attorney, Agent, or Firm*—Staas & Halsey

[57] ABSTRACT

A correlation detection type ultrasound blood flowmeter for measuring speed of flowing blood which is passing across two sample volumes which are respectively positioned at the same distance to each other from the blood flowmeter on two sound-beams formed by the blood flowmeter. The speed of flowing blood is measured by cross correlation time-difference detection, and the detection is performed by using sample and hold voltages obtained from echo signals reflected from the flowing blood which is passing across the two sample volumes. To the blood flowmeter, two quadrature detection circuits are applied for selecting echo signals reflected by the flowing blood from echo signals reflected by whole substances located along the two sound-beams by eliminating echo signals reflected by fixed substances located along the two sound-beams, and two range gate circuits are applied to each quadrature detection circuit for extending a range of each sound volume for measuring the speed of the flowing blood which passes across the two sample volumes not only perpendicularly but also aslant to a center line made by the directions of the two sound-beams.

8 Claims, 14 Drawing Figures

CORRELATION DETECTION TYPE ULTRASOUND BLOOD FLOWMETER

BACKGROUND OF THE INVENTION

The present invention relates to an ultrasound blood flowmeter of a correlation detection type for measuring speed of blood which flows almost perpendicularly to two ultrasound wave beams (sound-beams) formed by the ultrasound blood flowmeter. More particularly, the present invention relates to an ultrasound blood flowmeter of a correlation detection type (correlation detection type blood flowmeter).

Usually, a Doppler effect type blood flowmeter is used in measurement of the blood flow speed; however, the speed is merely a component in a sound-beam direction. In other words, a speed component perpendicular to the sound-beam cannot be measured by the Doppler effect type blood flowmeter, whereas the correlation detection type blood flowmeter can measure the speed of blood which flows perpendicularly to the sound-beam. The correlation detection type blood flowmeter was invented by the inventor of the present invention and its contents were disclosed in Japanese laid-open patent No. 58-71464 in 1983. Thus, the subject matter of the present invention relates to an improvement of the correlation detection type blood flowmeter. Therefore, before discussing the present invention, the prior art correlation detection type blood flowmeter will be explained with respect to FIGS. 1 and 2.

FIG. 1 is a schematic diagram illustrating a relation between sound-beams ($B_1$ and $B_2$) formed by a prior art correlation detection type blood flowmeter 101 (blood flowmeter 101) and a blood flow 301 or 302 in a blood vessel 311 or 312 (shown with dotted lines) located in a human body 300. The blood flowmeter 101 comprises an ultrasound transducer (transducer) TD put onto a body surface 303, wherein transducer TD forms dual sound-beams $B_1$ and $B_2$ for measuring the speed of blood flow 301 which flows almost perpendicularly to sound-beams $B_1$ and $B_2$, namely transducer TD sends pulsed or burst ultrasound waves (burst sound waves) into human body 300 along sound-beams $B_1$ and $B_2$ and receives echo signals reflected by substances located along sound-beams $B_1$ and $B_2$. Reference symbols $SV_{11}$ and $SV_{12}$ are referred to as sample volumes and they lie along sound-beams $B_1$ and $B_2$ respectively, and sample volumes $SV_{11}$ and $SV_{12}$ are equally positioned from transducer TD. The location of the flowing blood is determined by another ultrasound imaging means, and the positions of sample volumes $SV_{11}$ and $SV_{12}$ are adjusted so that blood flow 301 is caught by sample volumes $SV_{11}$ and $SV_{12}$.

FIG. 2 is an example of a block diagram of blood flowmeter 101. In the figure, reference numeral 13 is a ultrasound transducer which corresponds to transducer TD in FIG. 1. Transducer 13 is a multi-element array type ultrasound transducer which consists of an plurality of transducer elements and operates like a familiar phased array antenna of a radar system. Applying transducer 13 to blood flowmeter 101, blood flowmeter 101 may operate in two modes: a scanning mode (not illustrated) and a focusing mode. The former is used for providing ultrasound imagery, such as B-mode imagery, and the latter is used for measuring blood speed; the two modes can be easily changed by an electronic means. FIG. 2 shows a case of the focusing mode which forms two focused sound-beams $B_1$ and $B_2$; actually, a blood flowmeter according to the present invention can operate in combination with a unit for the scanning mode for imagery, but it is omitted in FIG. 2. A control unit 11 generates timing and sampling control signals. The timing signal is for controlling transducer 13 and a switching circuit 14, and the sampling control $V_S$ is for controlling sample-and-hold (S-H) circuits 22 and 23. Under the control of control unit 11, a drive unit 12 outputs driving pulses for driving transducer 13 to send burst sound waves out from the transducer elements of transducer 13, wherein the generated driving pulses are synchronized with the timing signals from control unit 11. The switching unit 14 is for switching transducer 13 so as to send the burst sound waves and to receive reflected sound waves under the control of control unit 11. When switching unit 14 is turned to T, as indicated in FIG. 2, the transducer elements send the sound wave bursts. After the burst sound waves are sent, switching unit 14 is turned to R, and then the transducer elements receive the reflected sound waves and convert them into electric echo signals (echo signals) respectively.

Echo signals transduced by transducer 13 are fed to amplifier elements of an amplifier 15 through switching unit 14 and fed to delay-line units 16 and 17. Delay-lines 16 and 17 correspond to sound-beams $B_1$ and $B_2$ respectively, each of which consists of delay-line elements which correspond to the transducer elements and compensate time differences of the received signals so that the echo signals received along sound-beams $B_1$ and $B_2$ can be simply added by adders 18 and 19 respectively. Thus, the technique for timing the relation between the control time of respective driving pulses and the delay-time of respective echo signals provides sound-beams $B_1$ and $B_2$. The technique is similar to phase array antenna technique of a radar system, namely the transducer elements are simultaneously driven, and the burst sound waves are transmitted to a rather broad area covering both sound-beams $B_1$ and $B_2$, while on the other hand, the receiving characteristics of the sound-beams $B_1$ and $B_2$ are made so as to be very sharp, respectively.

The echo signals added by adders 18 and 19 are fed to S-H circuits 22 and 23 through amplifiers 20 and 21 respectively. Each of S-H circuits 22 and 23 is of a conventional type, and echo signals respectively added by adders 18 and 19 are sampled at a sampling time $t_{s1}$ by a sampling control signal $V_S$ fed from control unit 11 and held. Sampling time $t_{s1}$ is determined by observing the location of the flowing blood, and sampling control signal $V_S$ is produced by a manual adjustment of control unit 11. The determination of sampling time $t_{s1}$ is equal to the determination of the positions of sample volumes $SV_{11}$ and $SV_{12}$. FIG. 3 shows a waveform chart illustrating the mutual time relation among the burst sound waves, the added echo signals, the sampling control signals, and the S-H voltages. FIG. 3($a$) is a train of the burst sound waves each of which bursts at time $t_0$ having period T; FIGS. 3($b$) and 3($c$) show the added echo signals with respect to sound-beams $B_1$ and $B_2$; FIG. 3($d$) shows a train of the sampling control signals each being generated at time $t_{s1}$ counted from each time $t_0$; and FIGS. 3($e$) and 3($f$) show S-H voltages $V_{SH1}$ and $V_{SH2}$ which correspond to sample volumes $SV_{11}$ and $SV_{12}$ respectively.

The S-H voltages $V_{SH1}$ and $V_{SH2}$ are fed to a time-difference detection circuit 24 which is for detecting a time difference between respective peak amplitude of S-H voltages $V_{SH1}$ and $V_{SH2}$ by cross correlation technique; FIG. 4 illustrates a relation of a cross correlation between the peak amplitude. As shown in FIG. 4, the amplitudes of S-H voltages $V_{SH1}$ and $V_{SH2}$ have respective peaks, which is due to the fact that blood has such a nature that it flows in a state of being gathered in small masses of red blood corpuscles. The amplitude variation depends on size of the respective mass. When blood flows almost perpendicularly to sound-beams $B_1$ and $B_2$ passing through sample volumes $SV_{11}$ and $SV_{12}$, the time-difference detection circuit 24 picks up peak amplitude $P_{11}$ and $P_{21}$ from S-H voltages $V_{SH1}$ and $V_{SH2}$ respectively by cross correlation and provides a voltage $V_{td}$ indicating the time difference between individual peak amplitudes $P_{11}$ ($P_{12}$, ---, or $P_{1n}$) and $P_{21}$ ($P_{22}$, ---, or $P_{2n}$), namely producing an output voltage called a time-difference voltage $V_{td}$. The time-difference detection circuit 24 comprises a fixed delay-line, a variable delay-line, and an automatic signal coincidence circuit; the details of which have been disclosed in Japanese laid-open patent No. 58-71464 in 1983 as mentioned before. The time-difference voltage $V_{td}$ is fed to a speed calculating circuit 25 in which the speed of blood which flows almost perpendicularly to sound-beams $B_1$ and $B_2$ passing through sample volumes $SV_{11}$ and $SV_{12}$ is calculated. The calculation is performed by dividing a distance between sample volumes $SV_{11}$ and $SV_{12}$ by time difference $t_{td}$; the distance can be previously obtained by determining the distance between transducer 13 and sample volume $SV_{11}$ or $SV_{12}$ and the angle (radians) between the sound-beams $B_1$ and $B_2$.

Thus, the correlation detection type blood flowmeter can measure the speed of blood which flows almost perpendicularly to the sound-beam; this is a great advantage compared with the Doppler type blood flowmeter which can measure only the speed of the blood in the direction of the sound-beam. However, in the prior art correlation detection type blood flowmeter, the sample volume $SV_{11}$ or $SV_{12}$ has almost no range, namely an undersirably small capability exists to detect the blood mass along the directions of sound-beam. Thus it has been very hard to detect the flowing blood, it being hard to adjust sample volumes $SV_{11}$ and $SV_{12}$ so as to catch the flowing blood. Further, the case often arises that the blood flows aslant to the sound-beam, as shown by blood flow 302 in FIG. 1. This has been a problem of the prior art correlation detection type blood flowmeter. Furthermore, a signal reflected by a fixed substance such as a blood vessel disturbs the detection of echo signals reflected by the flowing blood, which has been another problem of the prior art correlation detection type blood flowmeter.

SUMMARY OF THE INVENTION

An object of the present invention is to improve a correlation detection type blood flowmeter so that the blood flowmeter can measure the speed of flowing blood which flows not only perpendicularly to but also aslant to the respective sound-beam provided by the blood flowmeter.

Another object of the present invention is to improve the blood flowmeter so that the blood flowmeter can measure the speed of the flowing blood with high accuracy and reliability, by decreasing the disturbance due to echo signals reflected by fixed substances located along the sound-beam.

The above objects of the present invention are achieved by including a range gate circuit and a quadrature detection circuit in the blood flowmeter, the former being for increasing the practical range of a sample volume along the respective sound-beam, and the latter being for decreasing the disturbance from echo signals reflected by the fixed substances.

BRIEF DESCRIPTION OF THE DRAWINGS

FIG. 3 is a waveform chart for illustrating the functioning of the prior art correlation detection type blood flowmeter, wherein FIG. 3(a) is a waveform of burst sound waves, FIG. 3(b) is a waveform of an echo signal with respect to sound-beam $B_1$, FIG. 3(c) is a waveform of an echo signal with respect to sound-beam $B_2$, FIG. 3(d) is a waveform of a train of sampling control signals, FIG. 3(e) is a waveform of an S-H voltage with respect to sound-beam $B_1$, and FIG. 3(f) is a waveform of an S-H voltage with respect to sound-beam $B_2$;

DESCRIPTION OF THE PREFERRED EMBODIMENTS

Figure 1:
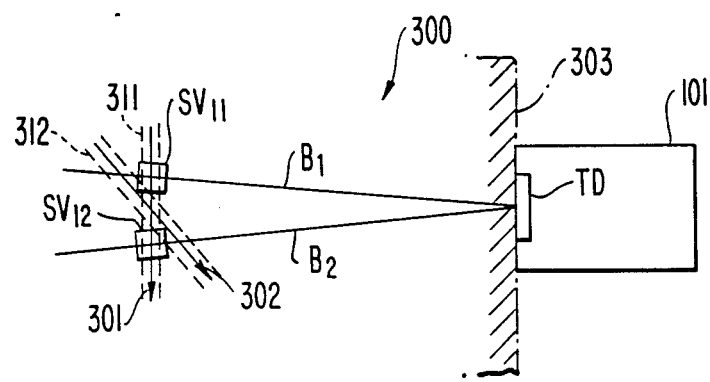
FIG. 1 is a schematic diagram illustrating an interaction between sample volumes, which are provided by the prior art correlation detection type blood flowmeter, and blood flow in two directions.
Figure 3:
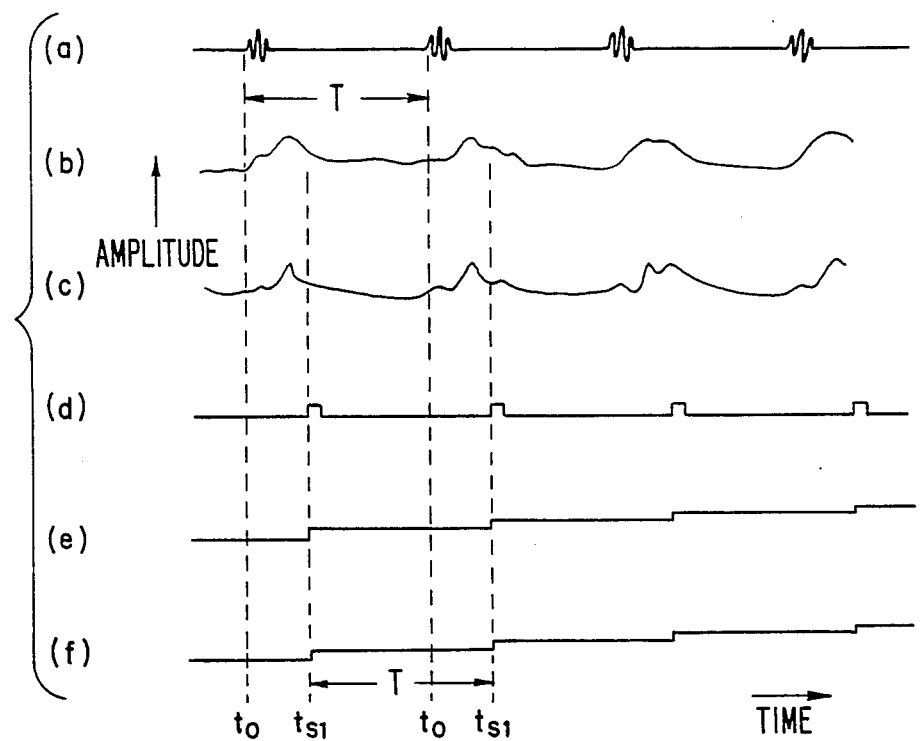
Figure 4:
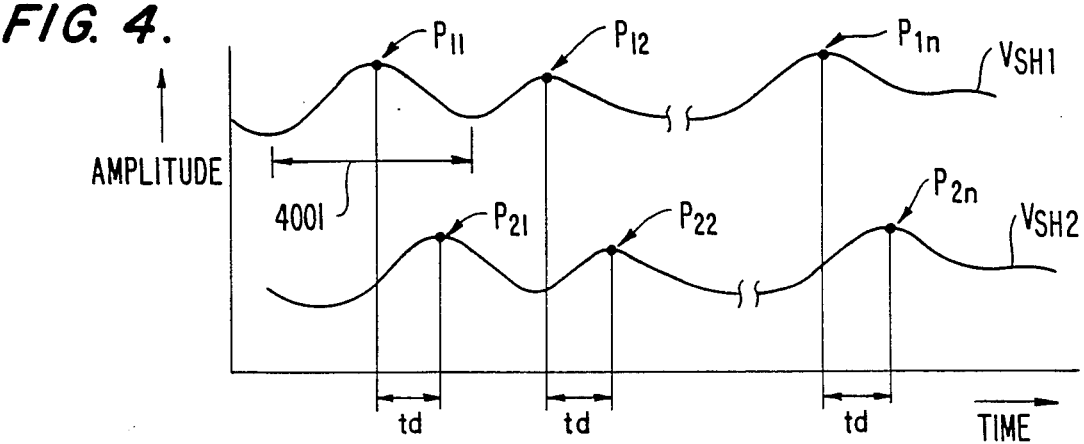
FIG. 4 is a waveform chart for illustrating a cross correlation between two S-H voltages.
Figure 2:
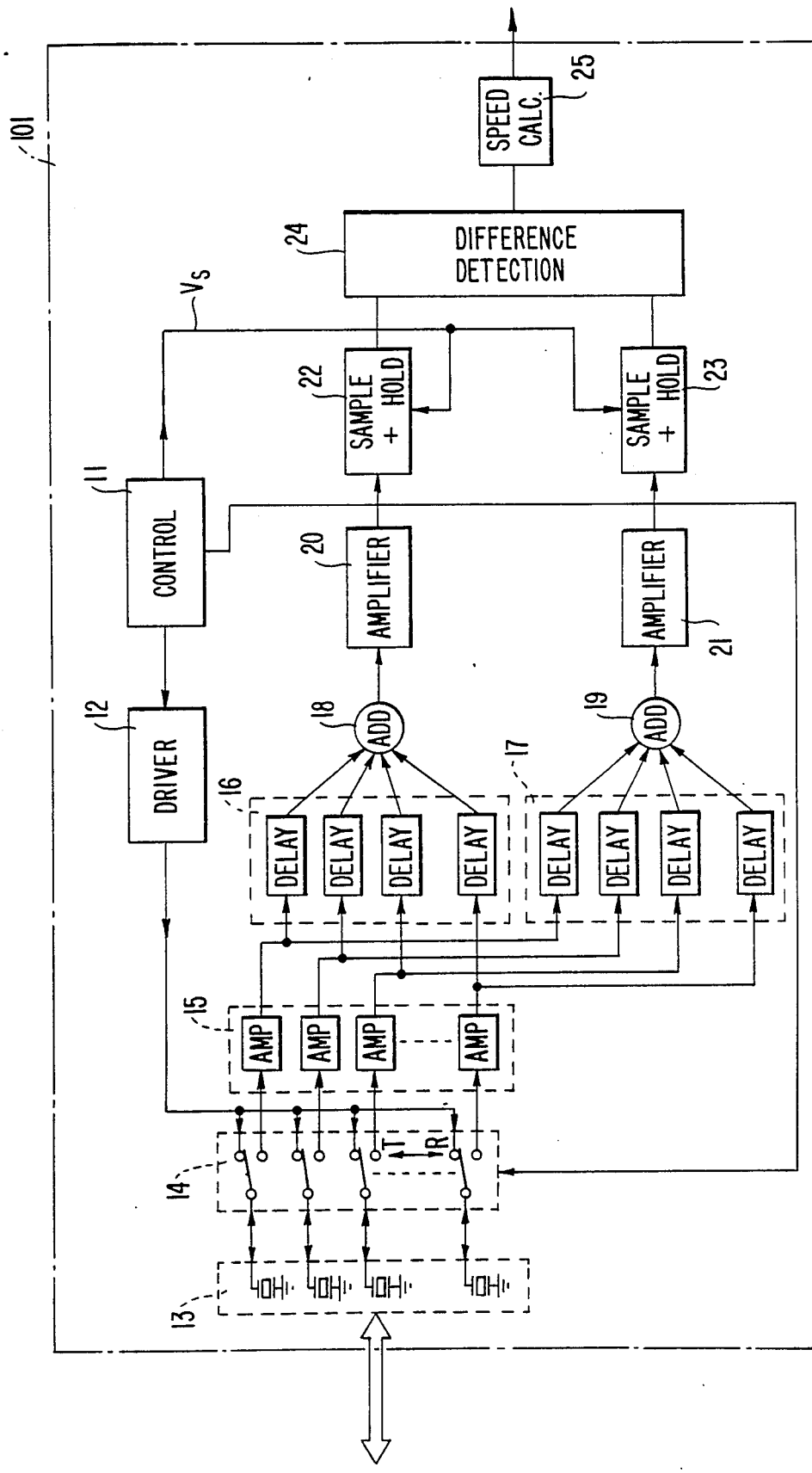
FIG. 2 is a block diagram of the prior art correlation detection type blood flowmeter.
Figure 5:
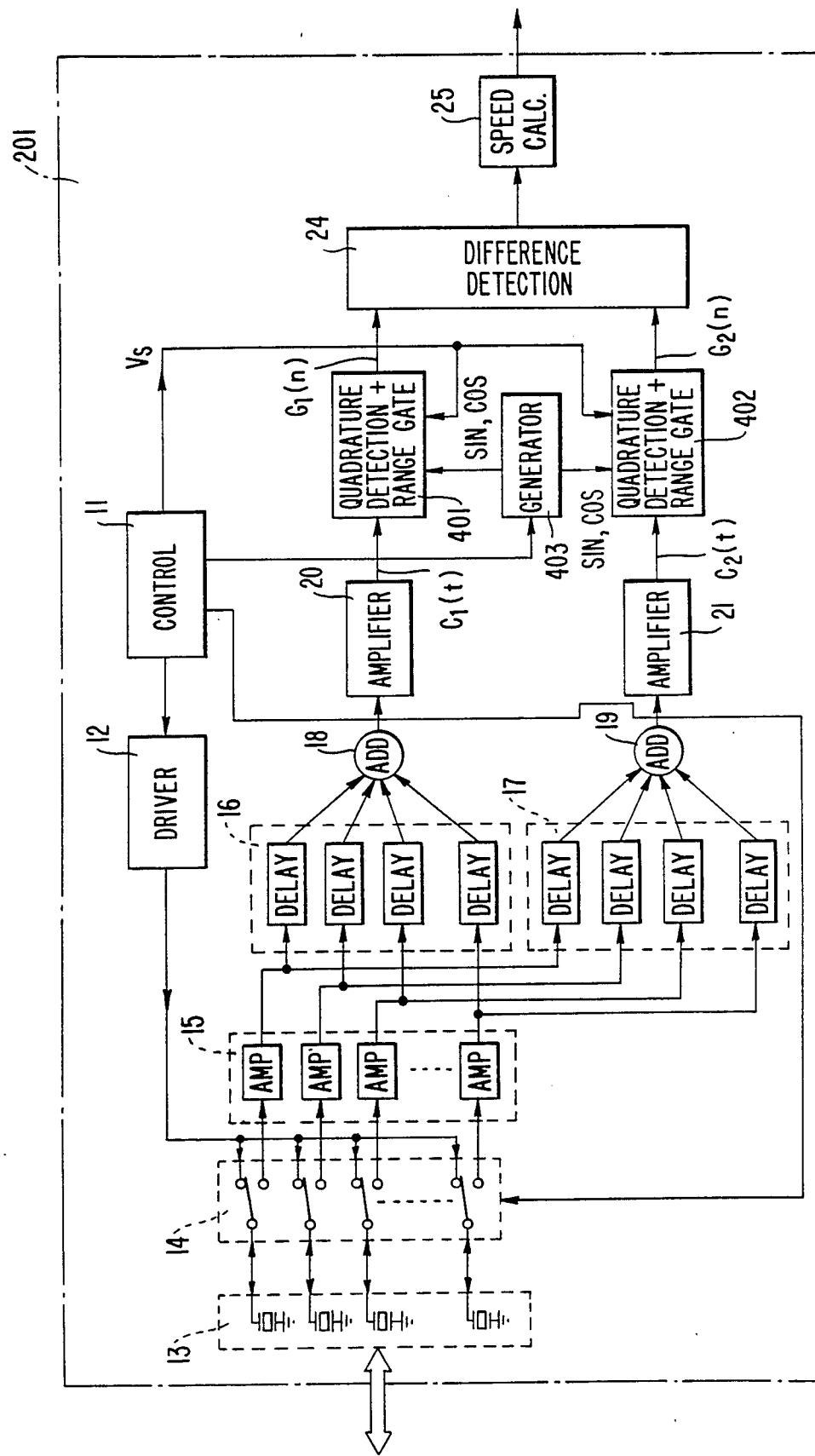
FIG. 5 is a block diagram of a correlation detection type blood flowmeter embodying the present invention.
Figure 6:
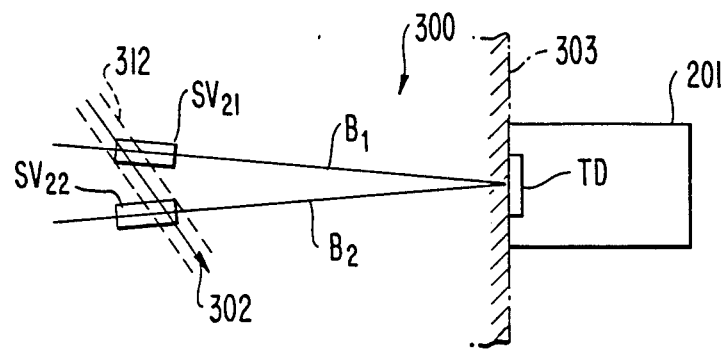
FIG. 6 is a schematic diagram illustrating an interaction between sample volumes, which are provided by a correlation detection type blood flowmeter embodying the present invention, and a blood flow.
Figure 7:
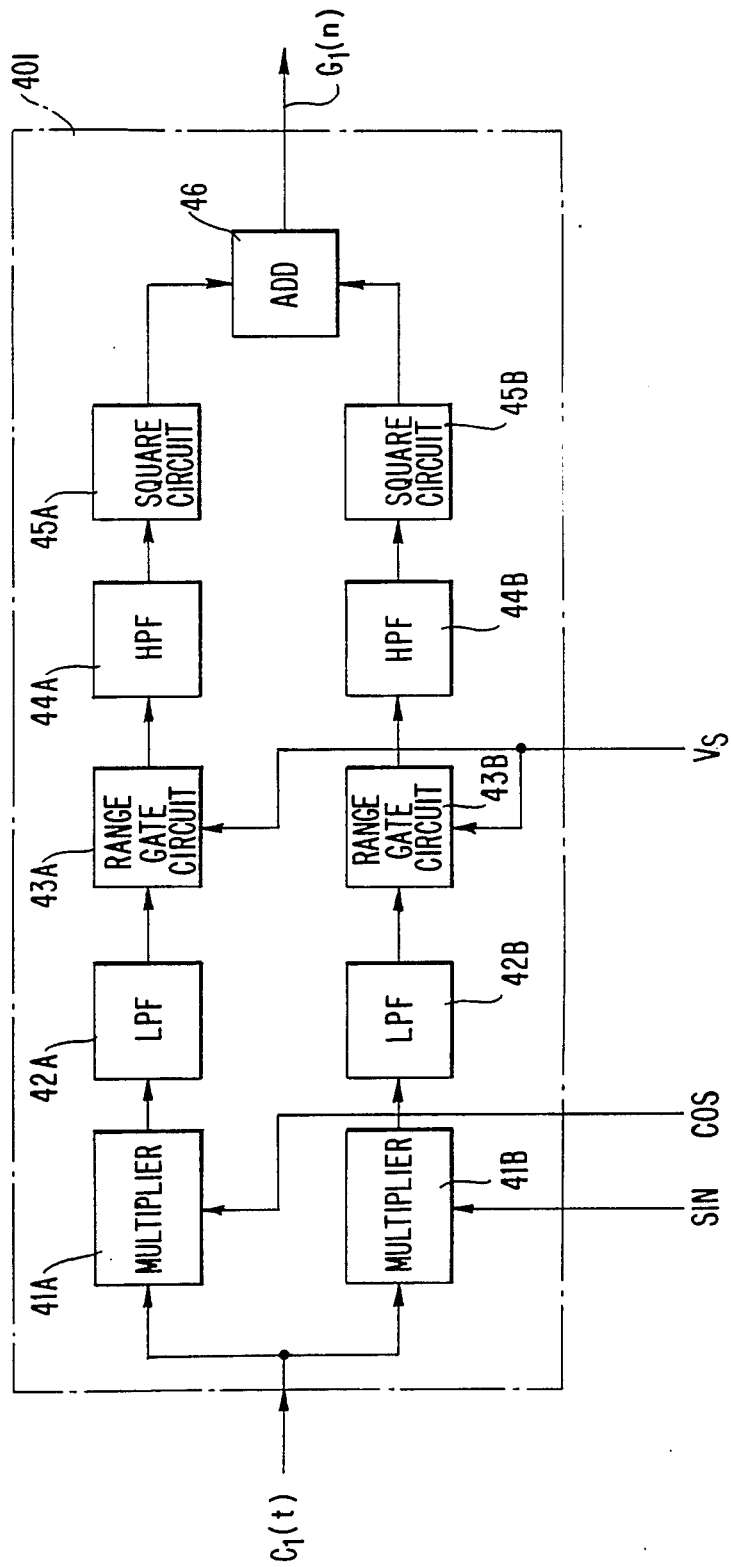
FIG. 7 is a block diagram of a detection & gate unit applied to a correlation detection type blood flowmeter embodying the present invention.

FIG. 5 shows a block diagram of a correlation detection type blood flowmeter 201 (blood flowmeter 201) embodying the present invention. In FIG. 5, each block with the same reference numeral as in FIG. 2 has the same function. The blood flowmeter 201 comprises two quadrature-detection and range-gate units (detection & gate units) 401 and 402 and a sine-cosine signal generator (sin-cos generator) 403. The detection and gate units 401 and 402 and sine-cosine generator 403 are for improving S-H circuits 22 and 23 of the prior art blood flowmeter 101 shown in FIG. 2. The detection and gate units 401 and 402 each have the same function, the former being for echo signals $C_1(t)$ received along sound-beam $B_1$ and the latter for echo signals $C_2(t)$ received along sound-beam $B_2$. FIG. 7 shows a block diagram of detection and gate unit 401 in which echo signals reflected by fixed substances located along sound-beam $B_1$ are eliminated by quadrature detection technique, and an echo signal reflected by flowing blood passing across sound-beam $B_1$ is gated over a relatively long range along sound-beam $B_1$ and sampled and held by a gated sample-and-hold technique; the long range corresponding to a sample volume such as $SV_{21}$ as shown in FIG. 6. Similarly, a sample volume $SV_{22}$ also can have a long range. Thus, the ranges of such sample volumes $SV_{21}$ and $SV_{22}$ can be extended respectively; accordingly, the speed of the blood can be measured even though the blood flows aslant to sound-beams $B_1$ and $B_2$, as shown in FIG. 6.

In FIG. 7, detection and gate unit 401 comprises two multipliers 41A and 41B, two low-pass filters 42A and 42B, two range gate circuits 43A and 43B, two high-pass filters 44A and 44B, and two square circuits 45A and 45B; and an adding circuit 46. In the above circuits, the range gate circuit 43A (43B) and high-pass filter 44A (44B) are for gated sample-and-hold, and the other parts are for quadrature detection.

When the burst ultrasound waves are sent into a body, an echo signal reflected by a fixed substance like a blood vessel is given by $$A(t) \cdot \sin(\omega_L t + \theta), \tag{1}$$

and an echo signal reflected from flowing blood is given by $$B(t + a_n) \sin(\omega t + b_n), \tag{2}$$

where, t: time,
A: amplitude function of an echo signal reflected by a fixed substance,
B: amplitude function of an echo signal reflected by flowing blood,
$\omega$: angular velocity of ultrasound transmitted in the body,
a: a factor of the Doppler effect,
b: a factor of flowing blood velocity,
n: respective number of sequential driving pulses, and
$\theta$: a phase difference concerned with the ultrasound reflected by the fixed substance.

When the echo signals presented by formulas (1) and (2) are superimposed, in view of actual echo signals having a state of being superimposed, the following echo signal C(t) is obtained by adding formulas (1) and (2):

$$C(t) = A(t) \cdot \sin(\omega t + \theta) + B(t + a_n) \cdot \sin(\omega t + b_n). \tag{3}$$

In formula (3), the necessary term for measuring the blood speed is a term $B(t + a_n)$; however, as seen in formula (3), it is impossible to determine the term $B(t + a_n)$ simply from formula (3). Rather, this term can be solved for by applying the technique of quadrature detection as follows.

Firstly, a sine signal and a cosine signal is multiplied with the echo signal C(t) so that following signals $D_1(t)$ and $D_2(t)$ are obtained:

$$D_1(t) = C(t) \cdot \sin \omega t \tag{4}$$

$$= A(t) \cdot \sin(\omega t + \theta) \cdot \sin \omega t +$$

$$B(t + a_n) \cdot \sin(\omega t + b_n) \cdot \sin \omega t$$

$$= A(t)(-\tfrac{1}{2} \cdot (\cos(2\omega t + \theta) - \cos \theta)) +$$

$$B(t + a_n)(-\tfrac{1}{2} \cdot (\cos(2\omega t + b_n) - \cos b_n)),$$

and $$D_2(t) = C(t) \cdot \cos \omega t \tag{5}$$

$$= A(t) \cdot \sin(\omega t + \theta) \cdot \cos \omega t +$$

$$B(t + a_n) \cdot \sin(\omega t + b_n) \cdot \cos \omega t$$

$$= A(t) \cdot \tfrac{1}{2} \cdot (\sin(2\omega t + \theta) + \sin \theta) +$$

$$B(t + a_n) \cdot \tfrac{1}{2} \cdot (\sin(2\omega t + b_n) + \sin b_n).$$

The sine and cosine signals are generated in sin-cos generator 403 and applied to detection and gate units 401 and 402 as shown in FIG. 5. The multiplication is made by multipliers 41A and 41B respectively as shown in FIG. 7, and the components with frequency $\omega$ and $2\omega$ are removed by low-pass filters 42A and 42B; hence, output signals from low-pass filters 42A and 42B; hence, output signals from low-pass filters 42A and 42B respectively become $$E_1(t) = \tfrac{1}{2} \cdot A(t) \cdot \cos \theta + \tfrac{1}{2} \cdot B(t + a_n) \cdot \cos b_n \tag{6}$$

and $$E_2(t) = \tfrac{1}{2} \cdot A(t) \cdot \sin \theta + \tfrac{1}{2} \cdot b(t + a_n) \cdot \sin b_n. \tag{7}$$

Secondly, the output signals $E_1(t)$ and $E_2(t)$ are fed to range gate circuits 43A and 43B respectively. The circuit and the operation of the range gate circuit 43A or 43B will be explained later; to sum up, signals $E_1(t)$ and $E_2(t)$ are sampled from a series of incoming echo signals at $t_{s1}$ ($t = T_{s1}$) in every driving pulse interval (in every n) within a gated time interval which corresponds to $SV_{21}$ and is held. As explained in connection with FIG. 2, the sampling time $t_{s1}$ is determined by the distance between transducer 13 and the flowing blood, and sampling control signal $V_S$ for sampling the echo signals at sampling time $t_{s1}$ is provided by control unit 11 and fed to detection and gate units 401 and 402 respectively as shown in FIGS. 5 and 7. The output signals of range gate circuits 43A and 43B are fed to high-pass filters 44A and 44B as shown in FIG. 7, and the first terms of formula (6) and (7) are removed, leaving the second terms; hence, output signals $F_1$ and $F_2$ of high-pass filters 44A and 44B become respectively $$F_1(n) = \tfrac{1}{2} \cdot B(t_{s1} + a_n) \cdot \cos b_n, \tag{8}$$

and $$F_2(n) = \tfrac{1}{2} \cdot B(t_{s1} + a_n) \cdot \sin b_n. \tag{9}$$

The output signals $F_1$ and $F_2$ are fed to square circuits 45A and 45B respectively and added in adding circuit 46; hence, the following square sum is obtained:

$$G_1(n) = \tfrac{1}{4} \cdot B^2(t_{s1} + a_n). \tag{10}$$

The square sum $G_1(n)$ consists only of the term $B(t_{s1} + a_n)$, in other words, the required term $B(t_{s1} + a_n)$, which is concerned with only the flowing blood, can be obtained.

Figure 8A:
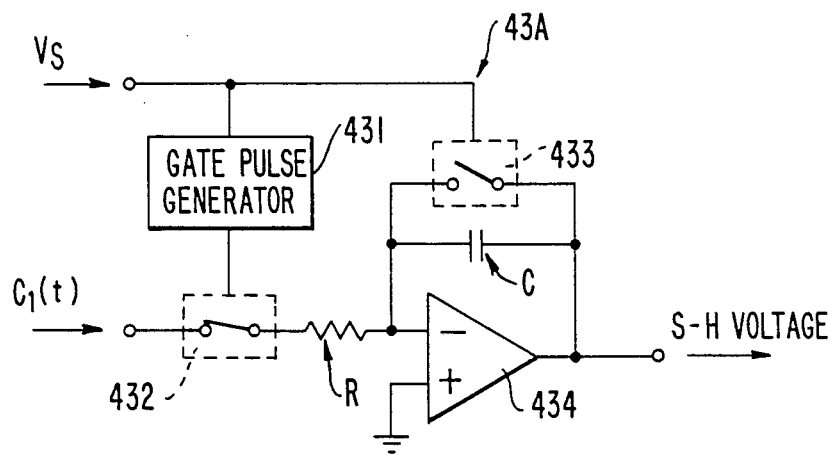
FIG. 8(a) is a circuit schematic diagram of a range gate circuit applied to a detection & gate unit of a correlation detection type blood flowmeter embodying the present invention.

FIG. 8(a) is a circuit schematic diagram of range gate circuit 43A which functionally consists of two circuits: a gated sampling circuit comprising a gate pulse generator 431, a switching element 432, and a switching element 433; and a holding circuit comprising an operational amplifier 434, a resistor R, and a capacitor C.

Figure 8B:
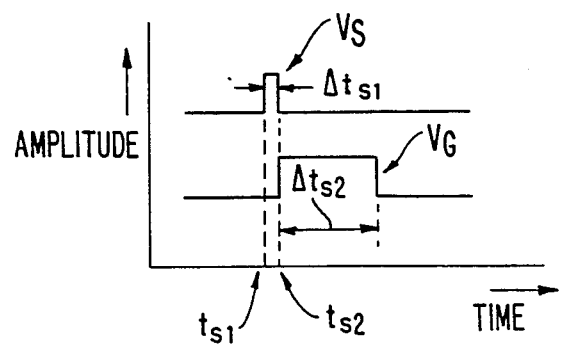
FIG. 8(b) is a waveform chart illustrating a function of a range gate circuit of a correlation detection type blood flowmeter embodying the present invention.

Range gate circuit 43A operates as follows when it receives sampling control signal $V_S$ from control unit 11. Just before sampling control signal $V_S$ is applied to range gate circuit 43A, switching elements 432 and 433 are OFF, so that an output voltage (S-H voltage) of range gate circuit 43A is a voltage charged on capacitor C. When sampling control signal $V_S$, which is a pulse having a pulse width (period) $\Delta t_{s1}$ as shown in FIG. 8(b), is fed to range gate control circuit 43A at time $t_{s1}$, switching element 432 is still OFF but switching element 433 becomes ON, so that the voltage which was charged on capacitor C is discharged; accordingly, the output of range gate circuit 43A becomes an initial potential. When sampling control signal $V_S$ is ended at time $t_{s2}$ as shown in FIG. 8(b), switching element 433 becomes OFF, and at the same time, gate pulse generator 431 generates a gate pulse $V_G$ having a pulse width (time duration) $\Delta t_{s2}$ and gate pulse $V_G$ is applied to switching element 432 so that switching element 432 becomes ON during time duration $\Delta t_{s2}$. Accordingly, the mean value of the echo signals of sound-beam $B_1$ is held at time $t_{s2}$ on capacitor C during time duration $\Delta t_{s2}$. Time duration $\Delta t_{s2}$ is a sampling time duration which corresponds to the range of sample volume $SV_{21}$, and the voltage charged on capacitor C is the S-H voltage of range gate circuit 43A. The S-H voltage is fed to high-pass filter 44A as shown in FIG. 7.

The echo signals $C_2(t)$ are processed by detection and gate unit 402 similarly to the case of detection and gate unit 401, and a square sum $G_2(n)$ is obtained. Square sums $G_1(n)$ and $G_2(n)$ are fed to time-difference detection circuit 24 in which a time difference between square sum $G_1(n)$ and square sum $G_2(n)$ is detected. The output of time-difference detection circuit 24 is fed to a speed calculating circuit 25 in which the speed of blood which flows through sample volumes $SV_{21}$ and $SV_{22}$ is calculated. The operation of time-difference detection circuit 24 and speed calculation circuit 25 in blood flowmeter 201 is similar to the operation of those in prior art blood flowmeter 101.

In the above discussion, blood flowmeter 201 is for measuring the speed of blood which flows perpendicularly or aslant to the sound-beams; however, in the above, the term "speed" is to be understood to mean "a component of speed that is perpendicular to the sound-beam", to be exact, because when blood flows aslant to the sound-beam, the direction of the blood speed is also aslant to the sound-beam. However, in the above discussion, the blood flowmeter 201 only measures "a component of speed that is perpendicular to the sound-beam".

The quadrature detection and correlation detection technique applied to blood flowmeter 201 can be used for measuring speed of blood which flows along a sound-beam. In this case, two sample volumes are properly positioned "along" the single sound beam. Each sample volume is not always necessary to be so long as that indicated above in connection with FIG. 2 for the range of the sample volume by used in blood flowmeter 201. Rather, the simple sample and hold technique can be used instead of the range gate circuit used in blood flowmeter 201, as done by the prior art blood flowmeter 101.

Accordingly, true speed of blood which flows aslant to the sound-beam can be obtained by calculating a vector sum of a horizontal speed component measured by blood flowmeter 201 and a vertical speed component measured by the above blood flowmeter or the prior art Doppler type blood flowmeter.

What is claimed is:
1. A correlation detection type ultrasound blood flowmeter for measuring speed of flowing blood in a body, comprising:
first means for repeatedly sending burst ultrasound waves toward two sample volumes, through which said blood is flowing, with a repetition frequency and for receiving echo signals along two lines from the body including echo signals from said flowing blood and fixed substances in the body, said two sample volumes being respectively positioned at the same distance from said blood flowmeter,
sine-cosine generator means for providing a sine signal and a cosine signal;
quadrature means for selecting respective ones of said echo signals, corresponding to said echo signals from said flowing blood passing through said two sample volumes, by eliminating said echo signals reflected by said fixed substances, said quadrature means including
multiplier means for multiplying said echo signals by said sine signal, for multiplying said echo signals by said cosine signal, and for providing output signals varying in response to said multiplications;
low pass filter means for filtering high frequency components of said output signals of said multiplier means and for providing the low pass filtered signals as filtered echo signals;
range gate means for extending a range of each of said two sample volumes by sampling and averaging said filtered echo signals in accordance with a gate pulse and for providing an output responsive to said sampling and averaging;
high pass filter means for filtering low frequency components out of said output of said range gate means and for providing the high pass filtered signals as filtered range signals;
squaring circuit means for squaring said filtered range signals; and
adding means for adding said squared filtered range signals and for providing added outputs responsive to said adding;
cross-correlation time difference detection means for cross-correlating said added outputs and for providing, based upon said cross-correlation, an output varying in accordance with the speed of said flowing blood in a direction substantially perpendicular to a line midway between said two lines.
2. A correlation detection type ultrasound blood flowmeter according to claim 1, wherein said quadrature means comprises two quadrature detection circuits and a sine-cosine signal generator, said sine-cosine signal generator is provided for applying both a sine signal and a cosine signal to each of said two quadrature detection circuits, each of said two quadrature detection circuits is provided for a respective one of said two sound-beams, and each said quadrature detection circuit comprises:
two multipliers for multiplying the respective echo signals reflected by said whole substances located along a respective one of said two sound-beams by said sine signal and said cosine signal, respectively, and for providing two respective outputs;
two low-pass filters for eliminating high frequency components included in said output signals of said two multipliers, respectively, and for providing the low frequency components thereof to said quadrature means as said respective parts of said echo signals corresponding to reflection from said flowing blood, respectively, said high frequency components including information on said fixed substances located along said two sound-beams, respectively, and for providing two respective outputs;

two high-pass filters for eliminating low frequency components of said respective outputs of said gate means, respectively and for providing respective outputs, said low frequency components containing information on said fixed substances located along said two sound-beams;

two square circuits for squaring said outputs of said two high-pass filters, respectively, and for providing respective outputs; and an adding circuit for adding said outputs of said two square circuits for producing a signal voltage containing information on said flowing blood located along each respective one of said two sound-beams, and for providing respective outputs for said cross-correllation time-difference detection.

3. A correlation detection type ultrasound blood flowmeter according to claim 1, wherein said range gate means comprises four range gate circuits, two of said four range gate circuits being inserted between said low-pass filter means and said high-pass filter means, each of said range gate circuits comprising:

a holding circuit comprising an operational amplifier, a resistor connected to an input terminal of said operational amplifier, and a capacitor connected between said input terminal of said operational amplifier and an output terminal of said operational amplifier, said output terminal being an output terminal of said range gate circuit; and a gated sampling circuit comprising a gate pulse generator means for generating said gate pulse, which has a first pulse width corresponding to said extended range of said two sample volumes, every time when a sampling control pulse signal having a second pulse width is applied to said gate pulse generator means, for designating the position of said two sample volumes along said two lines, with a repetition frequency equal to that for said burst ultrasound waves;

a first switching element for making an input connection for providing said outputs of said low-pass filter means to said resistor of said holding circuit when said gate pulse is applied to said first switching element during the occurrence of said first pulse width; and a second switching element for discharging said capacitor of said holding circuit before said gate pulse is applied to said first switching element.

4. A device for determining a value corresponding to the travel time for blood to flow in a blood vessel between two sample volumes in the blood vessel in a body, wherein said flowing blood contains inhomogeneities which cause associated changes in ultrasonic waves reflected from each of said two sample volumes when said inhomogeneities pass through said sample volumes; comprising transmitting and receiving means for transmitting bursts of ultrasonic waves of a first angular frequency into said body including said two sample volumes, and for receiving the corresponding ultrasonic waves relected from said two sample volumes and providing two corresponding outputs, gate and analysis means, coupled to said transmitting and receiving means, for controlling said transmitting and receiving means and for determining on the basis of said outputs therefrom said value corresponding to the time between said associated changes occur in the respective reflected ultrasonic waves from the same inhomogeneities of said blood passing through said two sample volumes, and for defining said two sample volumes in said body, wherein said gate and analysis means includes a respective signal path for each of said two outputs from said transmitting and receiving means, each said signal path including a respective pair of parallel signal lines; a first of said parallel signal lines of each of said pair thereof including a respective first means for multiplying a signal thereon by the sine function of the product of time and said first angular frequency of said transmitted ultrasonic waves; a low pass filter connected to an output of said first means for multiplying; a first gate circuit means, connected to an output of said first low pass filter, for determining the respective length of each of said two sample volumes by sampling and averaging the output of said first low pass filter; a first high pass filter connected to an output of said first gate circuit means; and a first squaring circuit coupled to an output of said first high pass filter for squaring a signal thereon, and the other of each of said pair of parallel signal lines including a second means for multiplying a signal thereon by the cosine function of said product of time and first angular frequency; a second low pass filter connected an output of said second means for multiplying, a second gate circuit means, connected an output of said second low pass filter, for determining the respective length of each of said two sample volumes by sampling and averaging the output of said second low pass filter; a second high pass filter connected to an output of said second gate circuit means; and a second squaring circuit coupled to an output of said second low pass filter, a respective adding means for receiving and adding respective outputs from said first and second squaring circuits of each of said signal paths and for providing summed squared outputs, and means, coupled to said respective adding means for cross-correlating said summed squared outputs, in order to compute said value corresponding to said travel time for said blood to flow between said two sample volumes.

5. The device of claim 4, said gate and analysis means comprising a respective range gate circuit connected at its output to a respective high pass filter in each said signal line, connected between the respective low pass filter and squaring circuits, wherein the respective length of each said sample volume in said body is determined by the respective range gate circuit.

6. The device of claim 4, wherein said value corresponding to the travel time indicates a component of a speed of the flowing blood in a direction substantially perpendicular to a plane extending from said transmitting and receiving means and spaced equally between said two sample volumes.

7. The device of claim 4, wherein said value corresponding to the travel time indicates a component of a speed of the flowing blood in a direction substantially perpendicular to a plane extending from said transmitting and receiving means and spaced equally between said two sample volumes.

8. The device of claim 4, wherein the output of each of said adding means substantially excludes information on any of said reflected ultrasonic waves reflected from any parts of said body in said two sample volumes that are not moving.

* * * * *

UNITED STATES PATENT AND TRADEMARK OFFICE
CERTIFICATE OF CORRECTION

PATENT NO. : 4,693,319

DATED : September 15, 1987

INVENTOR(S) : Shinichi AMEMIYA

It is certified that error appears in the above-identified patent and that said Letters Patent is hereby corrected as shown below:

Col. 1, line 55, change "a" to --an--;

line 58, change "an" to --the--.

Col. 5, line 51, change "a" to --the--.

Col. 6, line 32, change "$(t=T_{S1})$" to --$(t=t_{S1})$--.

Col. 10, line 35, after "ccnnected" insert --to--.

Signed and Sealed this

Thirty-first Day of May, 1988

Attest:

Attesting Officer

DONALD J. QUIGG

Commissioner of Patents and Trademarks